United States Patent [19]

Francesconi et al.

[11] Patent Number: 4,871,836

[45] Date of Patent: Oct. 3, 1989

[54] BORONIC ACID ADDUCTS OF RHENIUM AND RADIOACTIVE ISOTOPES OF RHENIUM DIOXIME COMPLEXES

[75] Inventors: Lynn C. Francesconi, Bridgewater, N.J.; Elizabeth N. Treher, Washington Crossing, Pa.

[73] Assignee: E. R. Squibb & Sons, Inc., Princeton, N.J.

[21] Appl. No.: 107,209

[22] Filed: Oct. 13, 1987

[51] Int. Cl.$^4$ .................... C07F 13/00; A61K 43/00; A61K 49/02
[52] U.S. Cl. ........................... 534/10; 424/1.1; 556/45; 556/37
[58] Field of Search .............. 534/10, 14; 424/1.1

[56] References Cited

U.S. PATENT DOCUMENTS

| | | | |
|---|---|---|---|
| 4,387,087 | 6/1983 | Deutsch | 424/1.1 |
| 4,419,339 | 12/1983 | Neirinckx | 424/1.1 |
| 4,434,151 | 2/1984 | Byrne et al. | 424/1.1 |
| 4,615,876 | 10/1986 | Troutner et al. | 534/14 X |
| 4,647,445 | 3/1987 | Lees | 424/1.1 |
| 4,652,440 | 3/1987 | Paik et al. | 424/1.1 |
| 4,659,839 | 4/1987 | Nicolotti et al. | 548/546 |
| 4,680,338 | 7/1987 | Sandoro | 525/54.1 |
| 4,705,849 | 11/1987 | Nunn et al. | 534/14 |
| 4,707,544 | 11/1987 | Jones et al. | 534/14 |
| 4,714,605 | 12/1987 | Feld et al. | 424/1.1 |

FOREIGN PATENT DOCUMENTS 0173629 3/1986 European Pat. Off. .

OTHER PUBLICATIONS

Edward Deutsch et al., "The Chemistry of Rhenium and Technetium as Related to the Use of Isotopes of these Elements in Kerapeutic and Diagnostic Nuclear Medicine", *Nucl. Med. Biol.* vol. 13, No. 4, pp. 465-477, *Int. J. Radiat. Appl. Instrum. Part B*, 1986.
Eckelman, W. C. and Levenson, S. M., "Radiopharmaceuticals Labelled with Technetium", *Int. Journal of Applied Radiation and Isotopes*, 1977, vol. 28, pp. 67-82. Pergammon Press.
Jackels, et al., Simple Direct Syntheses of Iron Clathro-chelates Derived from Dimethylglyoxime and Boron Compounds, 1972, JCS Chem. Comm., pp. 1291-1292.
Jackels, et al., Synthesis and Characterization of Clathro Chelates Derived from Iron(II), Dimethylglyoxime, and Boron Compounds, 1973, Inorg. Chemistry, vol. 12, pp. 1232-1237.
Robbins, et al., Synthesis and Electrochemistry of Iron-(II) Clathrochelates, 1985, Inorg. Chemistry, vol. 24, pp. 3381-3387.
Muller, et al., Synthesis and Characterization of a Ruthenium(II) 1986, Inorg. Chemistry, vol. 25, 2665.
Boston, et al., Synthesis and Study of Clathro Chelates Derived From Dimethylglyoxime, Cobalt and Lewis Acids, 1973, J. Amer. Chem. Soc., vol. 95, pp. 4163-4168.
Johnson, et al., {Tris[μ[(1,2-Cyclohexanedione Diozimato)-O O']Diphenyldiborato(2)---N,N',N",N''', N"",N""'}, 1983, Inorganic Synthesis, vol. 21, 112.
Jackels, et al., Iron(II) and Cobalt(III) Clathrochelates Derived From Dioximes, 1977, Inorg. Syntheses, vol. 17 pp. 139-147.
Deutsch, et al., Structural Characterization of a Bridged $^{99}$Tc-Sn-dimethylglyoxime complex; Implications for the chemistry of $^{99m}$Tc-radiopharmaceuticals prepared by the Sn(II) reduction of pertechnetate, 1976, Proc. Nat'l Acad. Sci., pp. 4287-4289.
Brechbiel, et al., Synthesis of 1-(p-Isothiocyanatobenzyl) Derivatives and DTPA and EDTA. Antibody Labeling and Tumor-Imaging Studies. 1986, Inorg. Chemistry, pp. 2772-2781.

*Primary Examiner*—Stephen J. Lechert, Jr.
*Assistant Examiner*—Virginia B. Caress
*Attorney, Agent, or Firm*—Donald J. Barrack; Stephen Venetianer

[57] ABSTRACT

Boronic acid adducts of radioactive isotopes of rhenium dioxime complexes are useful for labeling biologically active compounds as agents for radiotherapy. These boronic acid adducts of radioactive isotopes of rhenium dioxime complexes have the formula
I. ReX(Y)$_3$Z,
wherein
X is an anion;
Y is a vicinal dioxime having the formula
II.

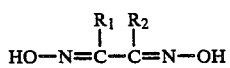

or a pharmaceutically acceptable salt thereof, and R$_1$ and R$_2$ are each independently hydrogen, halogen, alkyl, aryl, amino or a 5 or 6-membered nitrogen or oxygen containing heterocycle, or together R$_1$ and R$_2$ are —CR$_8$R$_9)_n$—wherein n is 3, 4, 5 or 6 and R$_8$ and R$_9$ are each independently hydrogen or alkyl;
Z is a boron derivative having the formula
III. B—R$_3$
wherein R$_3$ is hydroxy, alkyl, alkenyl, cycloalkyl, cycloaLkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl or arylalkyl, or R$_4$ and R$_5$ when taken together with the nitrogen atom to which they are attached form a 5 or 6-membered nitrogen containing heterocycle.

18 Claims, No Drawings

BORONIC ACID ADDUCTS OF RHENIUM AND RADIOACTIVE ISOTOPES OF RHENIUM DIOXIME COMPLEXES

BRIEF DESCRIPTION OF THE INVENTION

Boronic acid adducts of rhenium dioxime complexes incorporating radioactive isotopes of rhenium having the formula I. $ReX(Y)_3Z$, are useful for labeling biologically active compounds as agents for radiotherapy. In formula I, and throughout the specification, the symbols are as defined below X is an anion;

Y is a vicinal dioxime having the formula

II.

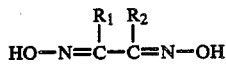

or a pharmaceutically acceptable salt thereof, and $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl;

Z is a boron derivative having the formula

III. $B-R_3$ wherein $R_3$ is hydroxy, alkyl, alkenyl, cycloalkyl, cycloalkenyl, alkoxy, carboxyalkyl (preferably having 2 to 19 carbons), carboxyalkenyl (preferably having 4 to 19 carbons), hydroxyalkyl, hydroxyalkenyl, alkoxyalkyl, alkoxyalkenyl, haloalkyl, haloalkenyl, aryl, arylalkyl or $(R_4R_5N)$alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle. Re includes $^{185}Re$, $^{186}Re$, $^{87}Re$ and $^{188}Re$ isotopes unless otherwise noted.

Listed below are definitions of the terms used to describe the complexes of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups. Additional exemplary aryl groups for instance wherein $R_3$ is aryl include 3-(5-dimethylamino-1-naphthalenesulfonylamino)phenyl, 3-[4-[3'-phenyl-2'-pyrazolin-1,1'-yl]benzenesulfonylamino]phenyl, 3-(pyrenesulfamido)phenyl, 3-[4-(4-dimethylamino-1-naphthylazo)-3(methoxyphenylsulfamido)]phenyl, 3-[4-(4-dimethylamino-1-phenylazo)-phenylthioureido]phenyl.

Preferred "cycloalkyl" and "cycloalkenyl" groups are those having 5, 6 or 7 carbon atoms. The terms include those groups substituted with alkyl, alkoxy, aryl, carboxyalkyl, arylalkyl or $(R_4R_5N)$-alkyl groups.

The terms "halide", "halo" and "halogen" refer to fluorine, chlorine, bromine and iodine.

The expression "5 or 6-membered nitrogen containing heterocycle" refers to all 5 and 6-membered rings containing at least one nitrogen atom. Exemplary aliphatic groups are dehydro derivatives of a compound having the formula

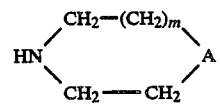

wherein m is 0 or 1 and A is O, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5 or 6-membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

The expression "5 or 6-membered nitrogen or oxygen containing heterocycle" refers to all 5 and 6-membered rings containing at least one nitrogen or oxygen atom. Exemplary groups are those described above under the definition of the expression "5 or 6-membered nitrogen containing heterocycle". Additional exemplary groups are 1,4-dioxanyl and furanyl.

DETAILED DESCRIPTION OF THE INVENTION

All of the examples and the following process description involve the use of "carrier rhenium" except as otherwise noted. The phrase "carrier rhenium" means that the rhenium compounds used contain non-radioactive rhenium at concentrations of $10^{-7}M$ to $10^{-5}M$.

Preparation of the complexes of this invention can best be accomplished using rhenium in the plus 3, plus 4, plus 5 or plus 7 oxidation state. Examples of compounds in which rhenium is available in the plus 3 oxidation state are $ReCl_3(CH_3CN)(PPh_3)_3$ and $[Re_2Cl_6](NBu_4)_2$ wherein Ph=phenyl and Bu=butyl. Re(IV) is available as $K_2ReCl_6$ and Re(VII) is available as $NH_4ReO_4$ or $KReO_4$. Re(V) is available as $[ReOCl_4](NBu_4)$ and $ReOCl_4(AsPh_4)$ and as $ReOCl_3(PPh_3)_2$ and as $ReO_2$(pyridine)$_4\oplus$. Other Re(III) Re(IV), Re(V), Re(VII) reagents known to those skilled in the art can also be used.

To prepare the complexes of this invention, the Re(III) Re(IV), Re(V) or Re(VII) ion (in the form of a salt) is combined with a source of anion, a boronic acid derivative having the formula

IV.

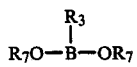

or a pharmaceutically acceptable salt thereof, wherein $R_7$ is hydrogen, alkyl or aryl, and a dioxime having the formula

II.

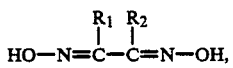

or a pharmaceutically acceptable salt thereof.

It is possible, in some instances, to prepare a boronic acid derivative of formula IV in situ. For example, when preparing a complex having an alkoxy group attached to the boron atom, it is possible to utilize boric acid and the appropriate alkanol as reactants.

The source of the anion moiety (X) can be water or it can be an acid or salt which dissociates to release an appropriate anion. Exemplary anionic moieties are hydroxyl, halide, isothiocyanato (N=C=S$^{\ominus}$) and thiocyanato (S—C=N$^{\ominus}$). The preferred anionic moieties are the halides, and chloride is the most preferred halide. If the source of the anion is not water, the source should be present in an appropriate concentration to compete effectively with any water that may be present during the reaction. It has been found that the source of anion should be present in the reaction mixture in a concentration of about 0.1 to 1.0 molar.

The boronic acid derivative of formula IV should preferably be present in a concentration of about 5 to 400 millimolar. The dioxime of formula II should preferably be present in a concentration of about 9 to 250 millimolar.

The formation of the complex proceeds best if the mixture of Re(III), Re(IV), Re(V), or Re(VII) ion, source of anion, boronic acid derivative, and dioxime is heated at about 25° C. to 50° C. for about 5 minutes to about 3 hours. The reaction is preferably run in an aqueous medium or aqueous alcohol mixture at a pH of less than, or equal to, about 5.

If Re(IV), Re(V), or Re(VII) containing compounds are employed, then the reaction mixture should also contain a reducing agent. Stannous ion is the preferred reducing agent, and can be introduced in the form of a stannous salt such as a stannous halide (e.g., stannous chloride or stannous fluoride). The reducing agent should be present in a concentration of about 10 millimolar to 150 millimolar.

When $^{186}$Re kits are prepared using radioactive $^{186}$Re, various complexing agents (also known in the art as chelating agents) can be included as part of the complexing reaction. The complexing agent should, of course, be pharmaceutically acceptable. Exemplary complexing agents are diethylenetriamine-pentaacetic acid (DTPA), ethylene glycol-bis($\beta$-aminoethyl ether)-N,N'tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., per cent of the radioactivity that is in the desired chemical form) of the product. Exemplary accelerators are the $\alpha$-hydroxycarboxylic acids such as citric acid, tartaric acid, and malonic acid.

It is convenient to prepare the complexes of this invention at, or near, the site where they are to be used. A kit having all of the components, other than the Rhenium ion, needed to prepare the boronic adducts of Rhenium dioxime complexes of formula I is an integral part of this invention. Such a kit contains a source of anion, a boronic acid derivative of formula IV (or compounds which can react in situ to form such a derivative), or a pharmaceutically acceptable salt thereof, a dioxime of formula II, or a pharmaceutically acceptable salt thereof, and a reducing agent. It may optionally contain a complexing agent.

The kits of this invention can be formulated in aqueous solution. The compounds are heated at about 100° C. for about 30 minutes. To optimize the stability of the kit, and to optimize the radiochemical purity of the labeled product, the pH of the kit should be adjusted to fall within the range of about 2.0 to 5.5 using a pharmaceutically acceptable acid or base (e.g., hydrochloric acid or sodium hydroxide). Preferably, the pH of the kit will be about 3.0. It is also preferred that the kit be in lyophilized form. While "wet" kits can be used, they are not as efficacious as the corresponding lyophilized kit. To isolate the desired complex, separation methods well known in the art are used.

The compounds of this invention are useful in radiotherapy. They are bonded to a specific entity such as a monoclonal antibody. This bonded entity is injected into humans and concentrates at the disease site, usually a malignant tumor. This allows for the targeting of radionuclides to cancer or tumor sites with great specificity. The methods of linking the compound to the antibody are well known in the art and are described in an article entitled "Synthesis of 1(p-isothiocyanatobenzyl) derivitives of DTPA and EDTA. Antibody Labeling and Tumor-Imaging Studies" by Martin W. Brechbiel, et.al. Inorganic Chemistry, 1986, 25, 2772.

Alternatively, the tris dioxime boronic acid ligand system provides the necessary features to label a biologically active molecule with a suitable radiotherapeutic isotope of Re: Re-186 or Re-188. The introduction of the biologically active molecule occurs at the boronic acid functionality. An example of this is the use of receptor binding molecules such as estrogens.

The complexes of this invention can be administered to a host by bolus intravenous injection at a concentration of 10 mCi–30 mCi. (millicuries).

The following examples are specific embodiments of this invention.

EXAMPLE 1

Re(chloride) (cyclohexanedionedioxime)$_3$butyl boron

ReCl$_3$(CH$_3$CN)(PPh)$_2$ (0.20 g, 0.23 mmol), cyclohexanedionedioxime, (0.123 amino-g, 0.87 mmol), and butylboronic acid, (0.032 g, 0.31 mmol) and a stir bar were placed in a 50 ml, 3 necked round bottom flask equipped with a condenser with a gas inlet valve. The apparatus was flushed with N$_2$ and CH$_2$Cl$_2$ (30 ml) was added by syringe. The mixture was heated and refluxed under N$_2$ for 15 hours. Gradually, the solution turned dark brown-orange. The remainder of the synthesis was done in air. The CH$_2$Cl$_2$ was removed by evaporation and acetonitrile was added to dissolve most of the resulting solid, some white undissolved solid was separated from the dark red solution and discarded. The CH$_3$CN was removed by evaporation and the resulting red solid was dissolved in CH$_2$Cl$_2$ and loaded onto a 15"×1.5" silica gel column prepared in CHCl$_3$. Elution with CHCl$_3$ gave one broad orange band. All other material adhered to the top of the column. This band was collected and evaporated to dryness to give 30 mg of orange solid or 15% yield of the title compound based on ReCl$_3$(CH$_3$CN) (PPh$_3$)$_2$. Crystals were obtained by cooling a boiling ethanolic solution of the orange solid to room temperature. They formed after several hours.

Elemental analysis: calc'd for ReClB-N$_6$O$_6$C$_{22}$H$_{35}$·½CH$_3$CH$_2$OH: C, 37.58; H, 5.21; N, 11.43; Cl, 4.82; Observed: C, 37.41; H, 5.14; N, 11.47; Cl, 4.84.

EXAMPLE 2

Re(chloride) (cyclohexanedionedioxime)$_3$ Methyl boron

ReCl$_3$(CH$_3$CN)(PPh$_3$)$_2$ (0.204 g, 0.24 mmol), cyclohexanedionedioxime (0.149 g, 1.04 mmol), and methylboronic acid (0.0465 g, 0.77 mmol) were placed in a 50 mL 3-necked round bottom flask fitted with a condensor, a nitrogen inlet tub, a stopper and a stir bar. The system was flushed with nitrogen. CH$_2$Cl$_2$ (30 mL) was added, the reaction mixture was slowly brought to a gentle reflux while stirring and a slight positive pressure of nitrogen was maintained. An additional 0.15 g (0.25 mmol) of methylboronic acid was added after about 1 hour. The reaction solution was gently heated for 22 hours. The reaction solution was loaded onto a silica gel column (2 cm×15 cm) and eluted with CH$_2$Cl$_2$. The orange brown band was collected, the product was concentrated by rotary evaporation (without heat) to about 1-2 mL. Methanol and dilute HCl were added. The crystalline red-brown solid was collected by filtration, washed with water and vacuum dried. Yield: 0.029 g, (29%). The HPLC (licrosorb C-18 column, 85% CH$_3$CN, 15% 0.1M ammonium acetate, UV detection at 250 nm) of this molecule shows a retention of 4.52 minutes.

Elemental analysis: calc'd for ReClC$_{19}$H$_{29}$N$_6$O$_6$B·½(CH$_3$CH$_2$)$_2$O: C, 34.99; H, 4.59; N, 12.25; Observed: C, 34.97; H, 4.17; N, 12.24.

EXAMPLE 3

Re(chloride) (cyclohexanedionedioxime)$_{butyl\ boron}$

NH$_4$ReO$_4$ (0.8 g, 3 mmol) dissolved in 10 ml concentrated HCl was added to a stirring solution of cyclohexanedionedioxime (3.0 g, 21 mmol) and butylboronic acid (1.3 g, 13 mmol) dissolved in 250 ml ethanol. To the resulting solution, 1.1 g SnCl (5 mmol) dissolved in 5 ml concentrated HCl was added dropwise. The resulting solution was stirred for one hour and gradually turned deep red. The solution was then evaporated to an oil (5-10 ml). Ethanol (20 ml) was added to dissolve the oil. To this stirring warmed solution, 30 ml of 1.5N HCl was added followed by 30 ml of H$_2$O to precipitate an orange solid. The solid was collected by suction filtration on a medium porosity sintered glass funnel, washed with 1.4N HCl (20 ml), then H$_2$O (20 ml). The solid was dissolved in ethanol (15 ml) and reprecipitated with dilute HCl (80 ml), washed with dilute HCl (40 ml) and dried in vacuo for 2 hours. Yield: 1.2 g orange solid, 56% based on NH$_4$ReO$_4$. The solid was totally dissolved in CH$_2$Cl$_2$ and loaded on a silica gel column (15"×1.5") and eluted with CHCl$_3$. The orange band was evaporated to dryness to give 110 mg of orange solid, 5% yield of the title compound based on NH$_4$ReO$_4$.

EXAMPLE 4

Re(chloride) (cyclohexanedionedioxime)$_3$ phenyl boron

Re(CH$_3$CN)Cl$_3$(PPh$_3$)$_2$ (0.396 g, 0.46 mmol), cyclohexane dionedioxime (0.265 g, 1.9 mmol), and phenylboronic acid, (Ph-B(OH)$_2$, 0.085 g, 0.70 mmol) were placed in a 50 ml three necked round bottom flask along with a teflon coated stirbar. The flask was flushed with nitrogen and then 40 ml CH$_2$Cl$_2$ was added by syringe. The reaction mixture was heated and refluxed under N$_2$ for ca. 12 hours. Gradually, the solution turned dark brown-orange. The remainder of the synthesis was done in air. The CH$_2$Cl$_2$ was removed by evaporation and acetonitrile was added to dissolve most of the resulting solid, some white undissolved solid was separated from the dark red solution and discarded. The CH$_3$CN was removed by evaporation and the resulting red solid was dissolved in CH$_2$Cl$_2$ and a portion of the solution was loaded onto a 7"×1" silica gel column prepared in CHCl$_3$. The column was eluted with CHCl$_3$ and an orange-red band was collected. This solution was evaporated to dryness to give an orange solid. The solid could be crystallized by cooling a boiling ethyl acetate solution of the orange solid to room temperature.

EXAMPLE 5

Re(chloride) (dimethyl gloxime)$_3$ butyl boron

Re(CH$_3$CN)Cl$_3$(PPh$_3$)$_2$ (0.38 g, 0.57 mmol), dimethylglyoxime, (0.20 g, 1.72 mmol), and butyl boronic acid (0.06 g, 0.59 mmol), and a stir bar were placed in a 50 ml 3 necked round bottom flask equipped with a condenser with a gas inlet valve. The apparatus was flushed with N$_2$ and 30 ml CH2Cl$_2$ was added by syringe and the mixture was heated and refluxed under N$_2$ for 15 hours. Gradually the solution turned a brown color. The CH$_2$Cl$_2$ was removed by evaporation and the resulting oily solid was dissolved in ethanol. HCl (15 mL, 0.6N) followed by 50 ml water was added to precipitate a black oil. This was dissolved in CH Cl$_2$ and the water layer was separated by centrifuging. The CH$_2$Cl$_2$ solution was deep red-brown in color and was dried with MgSO$_4$ The MgSO$_4$was filtered off. A small amount was loaded onto a silica gel column and eluted with CHCl$_3$. One band moved with the solvent front. This was collected and evaporated to dryness to give an orange-brown solid.

EXAMPLE 6

Re(chloride) (dimethylglyoxime)$_3$ butyl boron

K$_2$ReCl$_6$ (670 mg, 1.4 mmol) was added to 75 ml EtOH/H$_2$O (2:1), which contained dimethylglyoxime (654 mg, 5.6 mmol), butyl boronic acid (2.1 gm, 20 mmol) and LiCl (1.0 gm, 24.5 mmol). Solid stannous chloride (133 mg, 0.7 mmol) was added, and the solution was heated at 50° C. under N$_2$ for 3 hours. During this time, K$_2$ReCl$_6$ disappeared and the solution turned yellow-orange. The solution was stirred in air for 12 hours with no further change in reaction profile. During this time most EtOH evaporated. Nonpolar products were extracted into 50 ml of CH$_2$Cl$_2$. The orange organic layer was back-extracted with 25 ml of 0.1M HCl and stripped to dryness by rotary evaporation. The crude extract was dried in vacuo 0.3 torr for 12 hours to sublime off butyl boronic acid, redissolved in a minimal volume of CH$_2$Cl$_2$, and flash-chromatographed on a 2×8 cm silica gel column conditioned and eluted with CH$_2$Cl$_2$. The orange band was taken to dryness by rotary evaporation at room temperature to yield 10 mg (1.1%) of solid.

EXAMPLE 7

Re(chloride) (dimethylglyoxime)$_3$ butyl boron

Ammonium perrhenate (564 mg, 2.1 mmol) was dissolved in 20 ml of warm H$_2$O. It was added, with stirring, to a slurry of dimethylglyoxime (2.16 gm, 18.6 mmol) and butyl boronic acid (2.40 gm, 23.5 mmol) in 30 ml of boiling methanol. Four mmoles (765 mg) of $SnCl_2$ in 3 ml of 4M HCl was added dropwise over 1 minute with rapid stirring. The solution was then removed from heat, sealed under $N_2$ and stirred for 3 hours. The solution rapidly turned deep red-orange and a yellow-orange precipitate formed. Some dimethylglyoxine remained out of solution for the course of the reaction.

Water (20 ml) was added to the solution, and nonpolar products were extracted into $2 \times 25$ ml of $CH_2Cl_2$. The orange organic layer was dried over $MgSO_4$, filtered, and rotary evaporated to dryness at room temperature. The resultant red-orange solid was dried in vacuo at 0.3 torr for 12 hours to sublime off excess butyl boronic acid. It was then redissolved (incompletely) in 2 ml of $CH_2Cl_2$ and purified by flash chromatography on a $2 \times 8$ cm silica gel column that was conditioned and eluted with $CH_2Cl_2$. A red-orange band was collected. This band was evaporated under vacuum to dryness to give 36 mg of orange-brown solid, 3% yield of orange-brown microcrystalline title compound upon slow evaporation of a solution containing 5 mL methanol and 4 drops of 0.1M HCl.

EXAMPLE 8

Re(chloride) (glyoxime)$_3$ butyl boron

Glyoxime (267 mg, 2.97 mmol), butyl boronic acid (100 mg, 1 mmol) and $KReO_4$ (261 mg, 0.9 mmol) were stirred with 5 ml of 1M NaCl and 5 mL of MeOH. The solution was adjusted to pH 2.0 with 2M HCl and deoxygenated with $N_2$ for 10 minutes. Solid $SnCl_2$ (341 mg, 1.8 mmol) was added, and the solution stirred under $N_2$ for 2.5 hours. Then 2 mL of 2M HCl was added and the solution stirred for another hour. Nonpolar products were extracted into $2 \times 15$ ml of $CH_2Cl_2$ and stripped to dryness by rotary evaporation. The red solid was redissolved in a minimal volume of $CH_2Cl_2$ and chromatographed on a $2 \times 6$ cm silica gel column, which was conditioned with 90% CH MeOH and eluted with $CH_2Cl_2$. A yellow-orange band eluted rapidly and was evaporated to dryness to give 3.6 mg of red-brown title compound (0.7% yield). All other complexes were retained at the head of the column as a red-orange band.

Other rhenium starting reagents in oxidation states VI,V,IV may be useful. Some examples are $ReOCl_4[N-Bu_4]$, $ReO_2(pyridine)_4^+$.

Reducing agents other than stannous chloride may be employed to reduce Re in oxidation states VII, VI, V, and IV down to Re(III). Some examples include $NaBH_4$, $NaB(CN)H_3$, $NaS_2O_4$.

Extraction into organic solvents such as ether can be employed.

EXAMPLE 9

$^{186}$Re (chloride) (cyclohexanedionedioxime)$_3$ methyl boron and kit preparation To 0.5 ml of $H^{186}ReO$ dilute $HNO_3$ was added 0.5 ml of 0.5M $(Bu_4N)Br$ in dilute NaOH. The resultant solution was sorbed onto a Sep-Pak ($C_{18}$-silica), rinsed with one ml of $H_2O$ to remove $Na^+$ and $NO_3^-$. The $(Bu_4N)^{186}ReO_4$ was then displaced from the Sep-Pak with 1.2 ml of absolute ethanol. The $(Bu_4N)^{186}ReO_4$ was used to prepare the title compound in the following manner.

Approximately 10 mg stannous pyrophosphate was added to a freeze-dried kit containing 2 mg cyclohexanedionedioxime, 2 mg methylboronic acid, 50 µg $SnCl_2$, 100 mg NaCl, 9 mg citric acid, 2 mg DTPA, and 50 mg γ-cyclodextrin, as a solubilizer. The kit was reconstituted with 1 µmole of $(Bu_4N)^{186}ReO_4$ (ca 2–3 mCi) in 1 ml of saline, and then heated at 100° C. for 30 minutes. The pH of the kit was 3.7. This preparation resulted in about 18% yield of the title compound, as measured by HPLC, retention time=4.64 minutes in comparison to Example 2.

What is claimed is:

1. Boronic acid adducts of rhenium dioxime complexes which incorporate radioactive isotopes of rhenium having the formula

wherein X is an anion;
Y is a vicinal dioxime having the formula

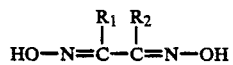

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —$(CR_8R_9)n$— wherein n is 3, 4, 5 or 6 and $R_8$ and $R_9$ are each independently hydrogen or alkyl; and
Z is a boron derivative of the formula

wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $(R_4R_5N)$-alkyl and $R_4$ and $R_5$ are each independently hydrogen, alkyl or arylallkyl, or $R_4$ and $R_5$ when taken together with the nitrogen atom to which they are attached form a 5 or 6-membered nitrogen containing heterocycle.

2. A boronic acid adduct in accordance with claim 1, wherein X is a halide.

3. A boronic acid adduct in accordance with claim 1, wherein X is chloride or bromide.

4. A boronic acid adduct in accordance with claim 1, wherein X is chloride.

5. A boronic acid adduct in accordance with claim 1, wherein Y is dimethyl glyoxime, 1,2-cyclohexanedione dioxime, 1,2-ethanedione dioxime, α-furyldioxime, 1,2-cyclopentanedione dioxime, or 3-methyl-1,2-cyclopentanedione dioxime.

6. A boronic acid adduct in accordance with claim 1, wherein Y is dimethyl glyoxime.

7. A boronic acid adduct in accordance with claim 1, wherein Y is 1,2-cyclohexanedione dioxime.

8. A boronic acid adduct in accordance with claim 1, wherein Y is 1,2-ethanedione dioxime.

9. A boronic acid adduct in accordance with claim 1, wherein Y is α-furyldioxime.

10. A boronic acid adduct in accordance with claim 1, wherein the boron derivative Z is B-alkyl.

11. A boronic acid adduct in accordance with claim 1, wherein the boron derivative Z is B-alkoxy.

12. A boronic acid adduct in accordance with claim 1, wherein the boron derivative Z is B-benzyl.

13. A boronic acid adduct in accordance with claim 1, wherein the boron derivative Z is B-cycloalkyl.

14. A compound according to claim 1 having the name Re (chloride) (cyclohexanedionedioxime)$_3$ butyl boron.

15. A compound according to claim 1 having the name Re (chloride) (cylohexanedionedioxime)$_3$ phenyl boron.

16. A compound according to claim 1 having the name Re (chloride) (dimethyl glyoxime)$_3$ butyl boron.

17. A compound according to claim 1 having the name Re (chloride) (glyoxime)$_3$ butyl boron.

18. A compound according to claim 1 having the name $^{186}$Re (chloride) (cyclohexanedionedioxime)$_3$ methyl boron.

* * * * *